(12) United States Patent
Steffen

(10) Patent No.: US 6,859,673 B2
(45) Date of Patent: Feb. 22, 2005

(54) CONFIGURABLE DEVICE AND METHOD FOR DISPENSING A SUBSTANCE

(75) Inventor: Beat Steffen, Saanen (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 10/207,347

(22) Filed: Jul. 29, 2002

(65) Prior Publication Data

US 2002/0177923 A1 Nov. 28, 2002

Related U.S. Application Data

(63) Continuation of application No. PCT/CH01/00035, filed on Jan. 17, 2001.

(30) Foreign Application Priority Data

| Feb. 1, 2000 | (DE) | ......................................... 100 04 314 |
| Aug. 3, 2000 | (DE) | ......................................... 100 37 893 |
| Oct. 18, 2000 | (DE) | ......................................... 100 51 576 |

(51) Int. Cl.[7] ............................................ G06F 17/00
(52) U.S. Cl. ........................... 700/90; 700/231; 604/67
(58) Field of Search .......................... 700/90, 95, 213, 700/231; 604/65, 67, 189, 232

(56) References Cited

U.S. PATENT DOCUMENTS

| 3,663,801 | A | * | 5/1972 | Wahli et al. ............ 253/462.04 |
| 5,651,775 | A | | 7/1997 | Walker et al. |
| 5,681,285 | A | | 10/1997 | Ford et al. |
| 6,171,276 | B1 | * | 1/2001 | Lippe et al. ................... 604/67 |
| 6,221,051 | B1 | * | 4/2001 | Hjertman et al. ........... 604/189 |
| 6,540,672 | B1 | * | 4/2003 | Simonsen et al. .......... 600/300 |
| 6,585,698 | B1 | * | 7/2003 | Packman et al. ........... 604/207 |
| 6,610,024 | B1 | * | 8/2003 | Benatti ...................... 604/4.01 |
| 2001/0044588 | A1 | * | 11/2001 | Mault ......................... 600/549 |
| 2002/0107477 | A1 | * | 8/2002 | Kipfer ......................... 604/67 |

FOREIGN PATENT DOCUMENTS

| FR | 2603488 | 3/1988 |
| WO | WO 84/00894 | 3/1984 |

\* cited by examiner

Primary Examiner—Paul Rodriguez
(74) Attorney, Agent, or Firm—Dorsey & Whitney LLP

(57) ABSTRACT

The invention relates to a device for dispensing a substance, in particular for self-administering a product fluid, wherein the device includes an operating system for controlling basic functions of the device and a memory unit for storing application-specific data, and encompasses a method for configuring the device. The invention also relates to a container for a substance including a coupling element for coupling the container to an administering device for administering the substance, wherein the container has an associated identifying element, and wherein the administering device includes a coupling device for accommodating the coupling element of the container and a sensor element for at least one of reading and writing the identifying element and the state of the container. The invention is intended to encompass methods for providing and using the identifying element.

16 Claims, 2 Drawing Sheets

CONFIGURABLE DEVICE AND METHOD FOR DISPENSING A SUBSTANCE

PRIORITY CLAIM

This application is a Continuation of International Application No. PCT/CH01/00035, filed on Jan. 17, 2001, which claims priority to German Application No. DE 100 04 314.3, filed on Feb. 1, 2000, German Application No. DE 100 37 893.5, filed on Aug. 3, 2000, German Application No. DE 100 51 576.2, filed on Oct. 18, 2000, all of which are incorporated by reference herein.

BACKGROUND

The present invention relates to a device and a method for dispensing a substance, for example, in one use or application, for self-administering a product fluid, e.g., insulin.

The invention also relates to a container for a substance, in particular a product fluid to be self-administered, and to a device for administering a substance.

Devices for dispensing substances wherein the device is adapted and used for a specific application or use, such as insulin treatment, at a particular dose, are known. In such cases, due to the specific application modalities, it is necessary to produce different dispensing devices for different areas of application having different task specifications.

Some devices for administering product take the form of portable infusion and injection devices, some of which are used in insulin treatment. Generally, such devices, including those used in insulin treatment, involve containers filled with the substance to be administered which are coupled to an administering device in order to dispense the substance contained in the container via the administering device to a patient. There are a multitude of substances which can be administered in this way, such as preparations comprising insulin for diabetes, growth hormones (hGH; human Growth Hormone) for disturbed growth, erythropoietine (Epo) for renal insufficiency or general lack of red blood corpuscles, alpha-interferone for hepatitis or cancer treatment, or potency-stimulating agents. Such containers, which are often geometrically identical, are often filled with different concentrations of the substance to be administered.

In order to reduce the danger of confusing containers having different substances, variously formed administering devices are known into which the respectively corresponding containers can be inserted.

A container is known from WO 98/00187 comprising a color coding which can be attached to it, consisting of a number of variously colored fields, wherein a property of a container or its contents can be identified by means of an optical sensor system.

SUMMARY

It is an object of the present invention to provide a device and a method for dispensing a substance, wherein the device and method can be used for a multitude of areas of application having different task specifications. Another object of the present invention is to provide a device and a method for dispensing a substance, wherein the device and method can be used for a variety of task specifications in a single area of application.

It is an object of the invention to provide a device and method for dispensing a substance wherein the device can be conveniently adapted to dispense a selected quantity of a selected substance.

In one embodiment, the invention comprises a device for dispensing a substance, wherein the device includes an operating system for controlling functions of the device and a memory unit for storing data, and encompasses a method for configuring the device.

In one embodiment, the invention comprises a device for dispensing a substance, for example, in one use or application, for self-administering a product fluid, wherein the device includes an operating system for controlling functions of the device and a memory unit for storing application-specific data, and encompasses a method for configuring or programming the device.

In one embodiment, the present invention comprises a device for dispensing a substance, for example, in one use or application, for self-administering a product fluid, wherein the device includes an operating system for controlling basic functions of the device and a memory unit for storing application-specific data. The present invention encompasses a method for configuring the device.

The device for dispensing substances in accordance with the invention, which can be used for self-administering a product fluid, e.g., as an infusion or injection device in insulin treatment, comprises an operating system for controlling basic functions of the device. The operating system is preferably a program stored in a writable or read-only memory associated with the device, wherein the program can be executed by a suitable processor or controller. This operating system, which may be designated as a BIOS (Basic Input Output System), is read from the memory when the device is activated, e.g., as or after a battery is inserted or the device is switched on, in order to perform a booting routine of the device. The operating system may be permanently introduced into the device as a ROM, or may be inserted in the device in the form of chip cards or memory sticks, and controls for input/output operations. Furthermore, a memory unit for application-specific data is provided. The memory unit can, for example, store various data for configuring the device depending on the intended use of the device, and, in some embodiments, data can also be read from the memory unit.

Procedures can be provided in the operating system, whereby the memory unit can be written on or programmed, and deleted again. Furthermore, various other procedures, including basis operational procedures, can be included in the operating system, such as procedures for triggering a series or parallel interface via which the application-specific data can be read into the memory unit. The interface can be formed as an electrical interface or as an optical interface, e.g., for exchanging IR signals. In some embodiments, it may also be possible to exchange signals telemetrically, i.e., via radio. In some embodiments, output functions, including elementary output functions, e.g., for initializing and writing on or triggering an LCD, can be included in the operating system.

Thus, in one embodiment in accordance with the invention, a fixed program section is provided in the device which can control basic functions of the device, such as elementary input and output functions. Another program or data section is designed to be freely configurable, such that procedures and/or data determined for specific applications (or uses, e.g., for delivering a selected substance or a selected quantity or dose of a substance) can be stored in it. Thus, it is possible to use a dispensing device which comprises basic procedures or settings which are necessary or desirable for a multitude of areas of application, wherein application-specific data, such as data with respect to the form or geometry of an ampoule or carpoule, can be predetermined for a particular application. This is advantageous because ampoules which have different dimensions or geometry, different contents or substances at different concentrations may be used in a single dispensing device. Furthermore, data specific to administrating can be set or selected, to define a standard quantity to be dispensed, a maximum permissible quantity to be dispensed, menu-guiding procedures, functional tests, optical or acoustic outputs, and the like. Thus, in accordance with the present invention, a dispensing device is provided which comprises certain basic functions, wherein the dispensing device can be configured for specific applications using additionally input data. The ability to configure or parameterize a general dispensing device in this way enlarges the range of application or uses of the device, since the hardware of such dispensing devices can remain the same while the software or particular memory elements may be exchanged or adapted for specific applications or uses.

In one embodiment, the memory unit is preferably formed as a writable memory unit, e.g., in the form of a general read/write memory in the form of a RAM, a flash memory or an EEPROM. A series or parallel interface is advantageously provided, via which data for configuring the device in accordance with the invention can be written into the writable memory unit using, for example, on an optical path using infrared light, electrical signals or telemetrically.

The memory unit may be advantageously formed as a separate, external memory medium which can be a known chip card, a memory stick or an optical or magnetic memory medium. Such a memory medium is preferably provided with a reading device, such that a chip card can be inserted into the reading device in order to appropriately configure the device in accordance with the invention using application-specific data stored on the chip card.

In general, therefore, a writable memory, a memory medium which can be inserted, or a combination of these two memory systems can be used to configure a dispensing device wherein the device and the selected memory system comprises general hardware or software for specific applications. In some embodiments, using a memory which may be freely programmed via an interface or a memory medium which may be inserted for specific configuration advantageously increases operational reliability and the capacity for multi-functionality and plural uses. Also, in some embodiments, since the operator no longer has to set or input anything on the device itself, which in the case of older or visually-impaired persons could lead to problems, dosing reliability, constancy and repeatability is advantageously increased. In some embodiments, wherein a user has the option to program the operating system, both multi-functionality, reliability and repeatability are enhanced.

In some embodiments, a system for identifying and/or correcting errors in data input or data transmission is advantageously provided, in order to be able to largely rule out possible malfunctions of the dispensing device. In this way, in one embodiment, known error correction codes can be used when transmitting application-specific data.

In some embodiments, a dispensing device in accordance with the present invention may comprise input elements on the device, such as one or more input keys or a touch screen, which gives an operator the opportunity to check and, as appropriate, alter input data, to re-configure the dispensing device, and/or to set specific operational modes.

In some embodiments, an ampoule or carpoule to be introduced into the device in accordance with the invention is advantageously provided with an identification marking, e.g., in the form of a barcode, which can be read by a reading device associated with or preferably provided on the dispensing device in order to activate or modify particular basic settings of the dispensing device. In this way specific data for an ampoule or carpoule can be read into the dispensing device. Such data might concern the substance contained in the ampoule or carpoule, its concentration, the inner diameter of the ampoule, or the specific sliding friction of the substance contained in the ampoule. This information can be used for dosing or for detecting errors, wherein, for example, a predetermined inner diameter of an ampoule, together with a specific sliding friction of a substance contained therein, can be used to determine a limit value for a counterforce generated by the ampoule when the substance is dispensed, so as to detect the presence of a blockage. Furthermore, data concerning a quantity of air in the ampoule or a minimum ventilating time can for example be read. In general, all the information specific to an ampoule or carpoule can also be stored in the memory unit, without a reading process for an inserted ampoule being necessary.

With respect to the design of an ampoule comprising an identification marking or a suitable identifying element, as well as to the design of a corresponding sensor element, reference is made to the Applicant's German patent application "Behlter und Vorrichtung zur Verabreichung einer Substanz" filed on Aug. 3, 2000, the teachings of which are incorporated herein by reference, the text of said German patent application having been translated into English and inserted into the present specification by amendment without adding new matter.

In accordance with one embodiment of the method for configuring a dispensing device in accordance with the present invention, in particular for self-administering a product fluid, application-specific data are firstly input into the device, wherein the substance is dispensed in accordance with the application-specific data input. In this way, a dispensing device with predetermined hardware can be configured for a multitude of areas of application or use, without changing the hardware.

With respect to the design of an ampoule comprising an identification marking or a suitable identifying element, as well as to the design of a corresponding sensor element, it is an object of the invention to provide a container for a substance to be administered, a device for administering the substance, and a method for detecting specific information concerning the substance contained in a container or the operational state of a container.

Other objects of the invention are to provide a container with a feature for providing at least one of container information or container contents information, to provide a method for providing the feature, and to provide a method for at least one of reading, remembering and changing the container information and container contents information.

In one embodiment, the present invention comprises a container for a substance, wherein the container comprises a coupling element for coupling the container to an administering device for administering the substance, wherein the container has an associated identifying element, and wherein the administering device includes a coupling device for accommodating the coupling element of the container and a sensor element for at least one of reading and writing the identifying element and the state of the container. The invention is intended to encompass embodiments of methods for providing and using the identifying element associated with the container.

The container for a substance in accordance with the invention comprises a coupling element, with which the container can be coupled to an administering device for administering the substance. If the container is coupled to an administering device, then the substance contained in the container can be dispensed by means of a piston or other suitable mechanism, preferably in a quantity which may be exactly dosed. In accordance with the invention, an identifying element assigned to the container is provided, which can contain information with respect to the substance contained and/or information with respect to the container itself. An identifying element in the sense of the present invention may be an individual element containing and/or providing a particular item of information or a plurality of elements containing and/or providing information, which can also be based on various physical principles. Such an identifying element can increase the operational reliability when using containers comprising substances to be administered. For example, it can be permanently stored or variably programmed into the administering device so that said administering device serves to administer a particular substance only, for example, a solution having a particular concentration of insulin. If a container with a different substance or concentration is accidentally used by the operator, then the identifying element in accordance with the invention can identify that a container which is unsuitable for the operator has been employed, and can, for example, block the dispensing of the substance or emit a corresponding warning signal. It is thus possible to produce an administering device which is suitable for a multitude of different possible applications, and which can reliably prevent unsuitable or damaging substances being dispensed in a given application. Thus, various systems of administering devices and corresponding containers do not have to be produced.

Furthermore, the identifying element in accordance with the invention can ensure for example that only original products can be dispensed using a particular administering device, if the identifying element is suitably formed to be adulterant-proof, e.g., cheap and poor-quality products can be identified and the substance in these products blocked from being dispensed.

The identifying element is preferably arranged on the container. Thus, the identifying element can for example be arranged in the area of a dispensing opening, in the area of the coupling mechanism, at a particular point on the container at a defined distance from the end of the container, or at any other suitable point. In this way, the identifying element may be arranged on the surface, in the casing wall of the container or in the interior of the container. In general, it is advantageous if there is a fixed connection between the identifying element and the container, so as to ensure that the identifying element is clearly assigned to a particular container.

It is also possible to assign an identifying element to a particular container without there having to be a fixed connection between the identifying element and the container. For example, a suitable identifying element can be included in the packaging for the container, e.g., a barcode printed on the packaging, a chip card enclosed with the packaging which for example may be broken off from a plastic card, such as is the example in packaging for mobile phones, or a magnetic card may be used. In general, any identifying element that can contain information and is suitable for specifying a substance contained in the container or a particular type of container would be suitable. This identifying element assigned to the container, such as a chip card, can then be inserted into the administering device, to release or transfer desired information to the administering device. Other ways of transferring the information stored by the identifying element are also conceivable, such as reading into the administering device a barcode or a magnetic strip associated with the packaging for a plurality of containers.

The identifying element is advantageously formed in such a way that information can be both read from the identifying element and also stored by the identifying element. In this way, for example, a magnetic strip arranged on the container can both store information with respect to the substance contained in the container and also be written on with particular information, such as when the container is repeatedly used, the time and/or quantity of the substance already dispensed from the container and the like. This can establish whether a container which since being used for the first time is no longer originally sealed has already been open too long, such that the substance contained in it has begun to degrade and should therefore no longer be dispensed.

The identifying element can preferably be formed as an element based on any one or more of electrical interaction, magnetic interaction, or capacitive and/or inductive interaction. Furthermore, the identifying element can also be based on mechanical principles.

It is possible to form the identifying element as an oscillating circuit, which for example is of a flat form printed onto a substrate, in order to read a particular item of information by way of the resonance frequency of the oscillating circuit. For example, an oscillating circuit with a resonance frequency of 10 kHz can be arranged on a container comprising insulin of a first concentration, an oscillating circuit of 20 kHz can be arranged on a container comprising insulin of a second concentration, etc. The contact elements of the oscillating circuit can be formed as mechanical contacts, or can be based on a capacitive or inductive coupling. The identifying element can be formed as a conductive structure, such as one or more surrounding elements arranged on the container, such as rings, spirals, or other suitable conducting patterns or structures. In this way, the conductive elements may be metal strips positioned on the surface of the container or metal which is vapor deposited onto a plastic container, wherein information can be obtained from the geometry of the conductive structure, i.e., from the number of rings surrounding the container or simply from the presence or absence of a conductor at a particular point on the container. The distance between different conductive structures may also be measured.

In some embodiments, it is furthermore possible to obtain particular information from the conductivity of the conductive structures, such that a container comprising a first substance is provided with low-resistance conductive structures and a container comprising a second substance is provided with high-resistance conductive structures. In this way, information may be obtained from the conductive structures by direct contact via electrodes, wherein capacitive or inductive couplings to the conductive structures are also possible, for example to obtain the desired information from a measured frequency response of a given metallic structure.

The identifying element can also be formed as an element based on optical effects. For example, a pattern of recesses at particular points may be introduced into the wall of the container, which can be optically detected and evaluated. Furthermore, reflective or light-defracting or light-refracting elements, for example a prism, can be arranged on the container. Using a prism, for example, a beam of light can be directed onto the prism, wherein the desired information is obtained from the deviation angle of the beam of light passing through the prism. If, for example, three different containers are to be distinguished from each other, then given a defined position of the prism, three light-sensitive elements can be arranged at different points, such that it is possible to distinguish the three containers simply using three different prisms.

It is furthermore conceivable to assign particular mechanical structures to the identifying element, such as protruding cams and/or recesses on the surface of the container, wherein, for a container inserted fixedly into the administering device, information can be obtained by a contact switch arranged at a particular point being pressed by a protrusion on the container wall or released by the absence of such a protrusion.

The identifying element is may be formed as a magnetic area which can be read from or written on, as with known credit cards or car-park tickets.

A magnetic strip enables information to be coded such that the magnetic strip serving as an identifying element is relatively secure against forgery and cannot easily be copied or decoded, in order to rule out misuse.

The identifying element may be designed as a chip, which likewise increases the security against forgery. It is equally conceivable to use a writable chip, for example to store information concerning the use which has already been made of a container on the chip.

The device in accordance with the invention for administering a substance comprises a coupling device which can be coupled to a coupling element of a preferably exchangeable container. In accordance with the invention, a sensor element is provided with which an identifying element and/or the operational state of a container, such as the insertion depth of a piston, can be read. The term sensor element in the sense of the invention includes at least both an individual sensor element and/or a plurality of sensor elements which can be based on the same or on different physical principles.

The sensor element is preferably formed such that an item of information contained in the identifying element described above can be read from them. Thus, the sensor element could be an oscillating circuit which emits signals at various frequencies, to determine the resonance frequency of an oscillating circuit serving as an identifying element, or in general to determine the frequency response of an identifying element. One or more electrical contacts can be used to determine the presence or absence of conductive structures, wherein a measuring device can be used to measure the electrical resistance, e.g., the actual impedance and/or the reactive impedance, in order to distinguish identifying elements of different conductivities. In general, identifying elements based on an electrical and/or magnetic principle can be read via direct electrical contacts or a capacitive or inductive coupling.

For detecting optical signals, a suitable optical sensor, such as for example a light barrier, a CCD element and possibly an assigned light source, is used. A daylight filter can be used to rule out undesired disruptive signals.

For detecting geometrical structures containing a spatial structure or information, a positional sensor can be used, in particular a switch which is pressed or released according to the respective presence or absence of a protrusion.

If magnetic identifying elements are used, then Hall sensors or other suitable reading heads can be used to read the magnetic identifying elements.

If a chip is used as the identifying element, then a processor is preferably provided which may be coupled to the chip, and which can read information from the chip or store information in the chip. It can be coupled to the chip for example directly, via sliding contacts, or without contact, capacitively or inductively.

In general, a processor or suitable switching circuit is preferably provided which is coupled to the sensor element, to read and/or evaluate information contained in the identifying element.

A writing device is advantageously provided in the device in accordance with the invention for administering a substance, said writing device writing information onto a container coupled to the administering device. Information may also be written directly into a specific identifying element. It is, however, also possible to write information onto the identifying element in another way, such as by attaching a colored marking or forming a slight recess in the container wall, to store particular information assigned to the container or to attach suitable markings for the container.

A transport device is advantageously provided for the container, using which a container coupled to the administering device can for example be slowly drawn into the administering device once they have been successfully coupled. Such a retracting device can be designed such that a container is moved past a sensor element at a predetermined speed or is positioned in relation to the sensor element, so as to ensure a desired interaction between the sensor element and an identifying element on the container.

The sensor element is advantageously formed such that externally inputted identifying elements can also be detected, such as for example chip cards separated from the container and sold or provided together with the container or barcodes arranged on the packaging of a container, in general, any of the sensor elements described above can be used on its own or in combination, such that container-specific information can be read directly via identifying elements arranged on the container, wherein additional information concerning, for example, the operator of the administering device and/or prescribed medication can be stored in the administering device via external elements to be read in. In this way, for example, a physician can store the course over time and the dosage of a medication on a magnetic card and hand this magnetic card over to the patient, wherein the patient inserts this magnetic card into his administering device in order to store the prescribed treatment.

The invention further relates to a system comprising an administering device having one or more of the features described above, and to a container for a substance having one or more of the features described above.

In accordance with the method in accordance with the invention, a specific item of information for a container or its contents is detected by coupling the container to an administering device and reading an identifying element assigned to the container. The information read is preferably stored in the administering device, wherein the profile or a prescribed treatment for an operator can additionally be stored. The information stored and/or read in this way can then be used to dose and/or administer a substance. Furthermore, as explained above, it is possible to use such information to configure a device for administering and/or dispensing a substance.

DETAILED DESCRIPTION

Figure 1:
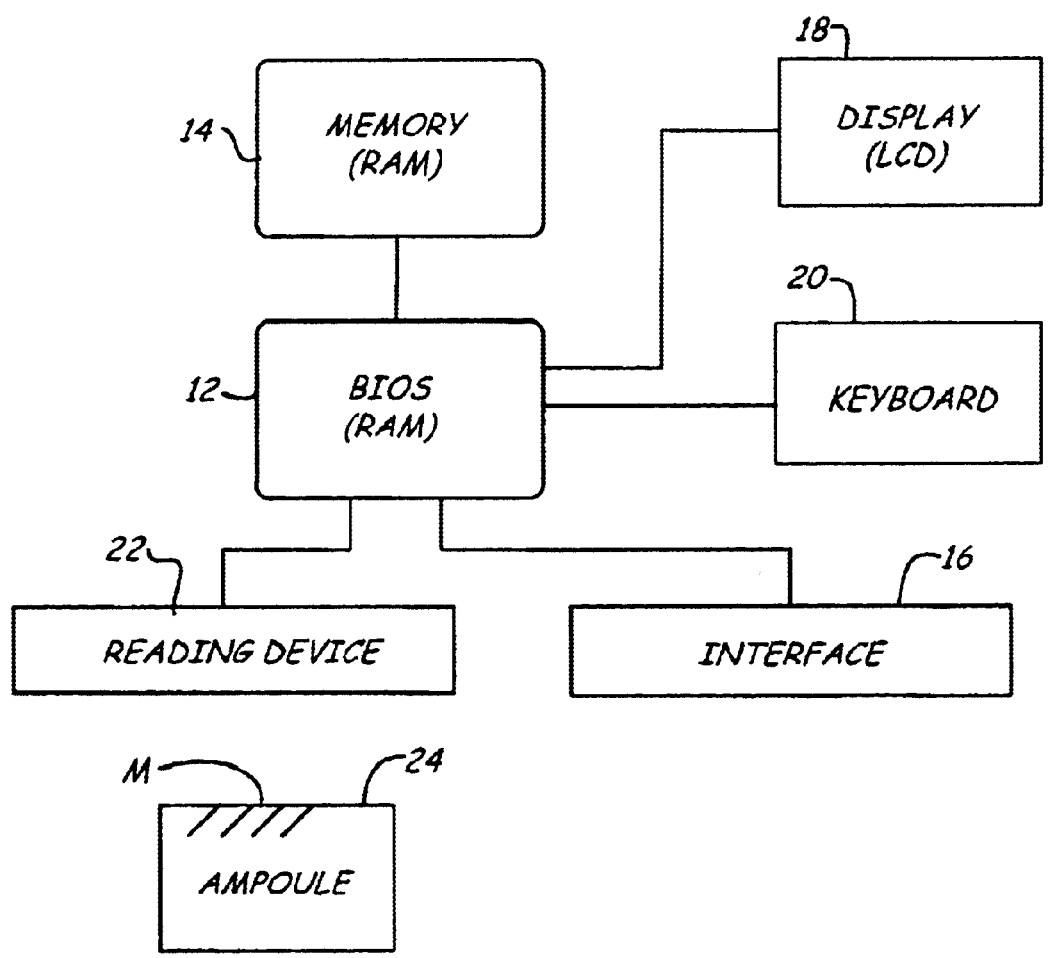
FIG. 1 schematically depicts an embodiment of the present invention.

FIG. 1 depicts an exemplary embodiment of functional elements of one embodiment of the deice for dispensing a substance in accordance with the present invention, wherein an operating system (BIOS) is stored in a ROM 12. Data for configuring the device can be written into the memory (RAM) 14 via an interface 16 connected to the operating system, wherein said data can also be retrieve from the memory and output to the interface or a display 18. Furthermore, specific data, e.g., configurations of the device can be set via an input such as a keyboard 20. A reading device 22 connected to the operating system is able to identify a marking "M" attached to an ampoule 24 in order to be able to automatically activate particular settings specific to the ampoule, its contents and/or the use of the device. By way of an example, the marking "M" is shown in FIG. 1 as a barcode. A system 26 for identifying and/or correcting errors in data input or data transmission may be operably coupled to the operating system in order to be able to largely rule out possible malfunctions of the dispensing device.

Figure 2:
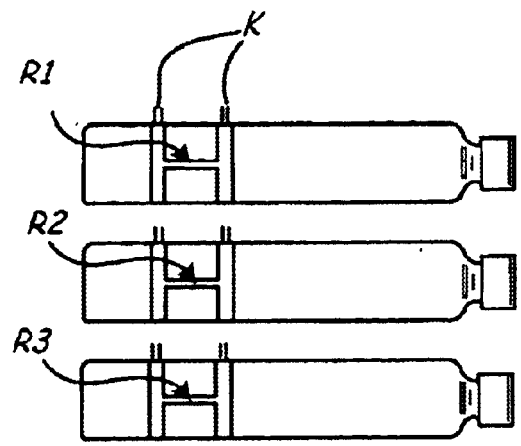
FIG. 2 depicts a first examplary embodiment for characterizing three different ampoules using three different resistances R1 to R3 and using two contacts.

As can be seen from FIG. 2, three ampoules having the same container geometry but different concentrations of the medications contained in them can be coded by using different resistances, such as the resistances R1, R2 and R3. In this way, an electrical contact having the respective resistances can be established at a fixedly predetermined point relative to the container geometry via two contact elements "K" arranged on a device for administering a substance, e.g., a pen. If an ampoule is inserted into a pen, then once contact has successfully been made, the resistance value can be determined, and from this resistance value it can be determined what medication is contained in the ampoule and/or what the concentration of a particular medication is.

Figure 3:
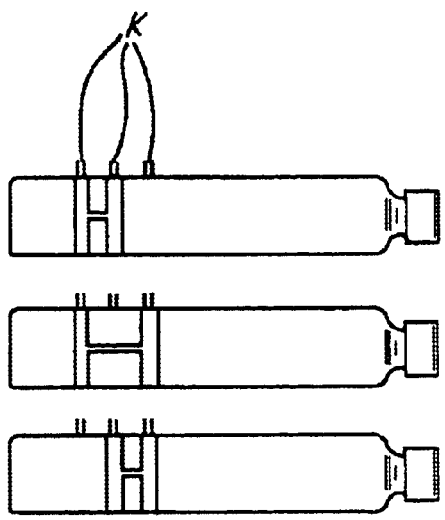
FIG. 3 depicts coding three different ampoules by positioning a strip conductor comprising three contacts.

FIG. 3 shows a second embodiment of the invention, in which three ampoules are coded using conductive structures in various positions. Contacts "K" are required to determine a specific ampoule 3. As can be seen from FIG. 3, in the case of an inserted ampoule, which ampoule has been inserted can be determined by electrically connecting two contacts. Thus, for example, the left-hand and center contacts on the ampoule shown at the top of FIG. 3 are electrically connected to each other, with no connection to the right-hand contact, such that a pen can determine by way of this electrical connection between the contacts, which ampoule has been inserted.

Figure 4:
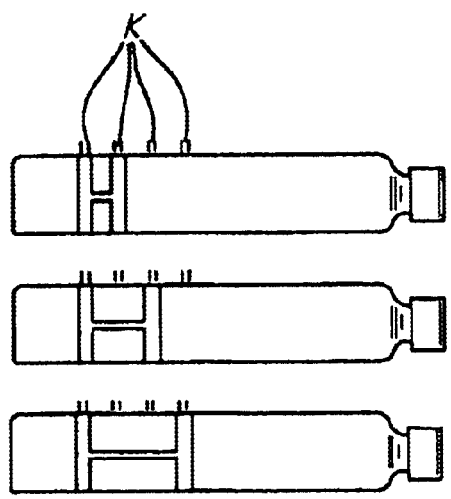
FIG. 4 depicts coding three different ampoules by means of a strip conductor using four contacts.

FIG. 4 shows a third embodiment, in which four contacts are used in order to identify a conducting pattern on an inserted ampoule. Depending on the ampoule inserted, the left-hand contact is connected to one of the remaining three other contacts, such that a pen can determine the specifically inserted ampoule.

In the foregoing description a preferred embodiment of the invention has been presented for the purpose of illustration and description. It is not intended to be exhaustive or to limit the invention to the precise form disclosed. Obvious modifications or variations are possible in light of the above teachings. The embodiment was chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for dispensing a substance, in particular for self-administering a product fluid, comprising:

a) an operating system for controlling basic functions of said device;

b) a memory unit operably coupled to the operating system for storing and reading in application-specific data; and c) a reading device operably coupled to the operating system, wherein said reading device is adapted to identify an ampoule or carpoule;

wherein the ampoule or carpoule carries data concerning a quantity of air in the ampoule or carpoule.

2. The device as set forth in claim 1, wherein said memory unit is writable.

3. The device as set forth in claim 1, further comprising an interface operably coupled to the operating system and to the memory unit for communicating with said memory unit.

4. The device as set forth in claim 1, wherein said memory unit comprises an external memory medium.

5. The device as set forth in claim 4, wherein said memory unit comprises a chip card.

6. The device as set forth in claim 4, wherein said memory unit comprises a memory stick.

7. The device as set forth in claim 1, wherein said reading device can read an external memory medium.

8. The device as set forth in claim 1, further comprising an error identifying and correcting device operably coupled to the operating system.

9. The device as set forth in claim 8, wherein said error identifying and correcting device is adapted to identify and correct at least one of input errors and transmission errors.

10. The device as set forth in claim 1, further comprising a data input device operably coupled to the operating system.

11. The device as set forth in claim 10, wherein said data input device comprises a keyboard.

12. The device as set forth in claim 10, wherein said data input device comprises a touch screen.

13. The device as set forth in claim 10, wherein said data input device is provided on said device.

14. A device for dispensing a substance, in particular for self-administering a product fluid, comprising:

a) an operating system for controlling basic functions of said device;

b) a memory unit operably coupled to the operating system for storing and reading in application-specific data; and c) a reading device operably coupled to the operating system, wherein said reading device is adapted to identify an ampoule or carpoule;

wherein the ampoule or carpoule carries data concerning a minimum ventilating time associated with the ampoule or carpoule.

15. The device as set forth in claim 14, wherein the ampoule or carpoule carries data concerning a diameter of the ampoule or carpoule and a sliding friction of a substance contained in the ampoule or carpoule.

16. The device as set forth in claim 15, wherein said reading device comprises a barcode reading device.

* * * * *